(12) United States Patent
Heggeness (10) Patent No.: US 6,699,242 B2
(45) Date of Patent: Mar. 2, 2004

(54) METHODS AND DEVICES FOR INTRAOSSEOUS NERVE ABLATION

(75) Inventor: Michael H. Heggeness, Houston, TX (US)

(73) Assignee: Baylor College of Medicine, Houston, TX (US)

(*) Notice: Subject to any disclaimer, the term of this patent is extended or adjusted under 35 U.S.C. 154(b) by 214 days.

(21) Appl. No.: 09/775,137

(22) Filed: Feb. 1, 2001

(65) Prior Publication Data

US 2001/0047167 A1 Nov. 29, 2001

Related U.S. Application Data

(60) Provisional application No. 60/179,959, filed on Feb. 3, 2000.

(51) Int. Cl.$^7$ ............................................. A61B 18/18
(52) U.S. Cl. ......................................... 606/41; 606/45
(58) Field of Search ................. 607/117, 118; 606/41–52, 170, 180

(56) References Cited

U.S. PATENT DOCUMENTS

| | | | |
|---|---|---|---|
| 4,044,774 A | | 8/1977 | Corbin et al. |
| 4,573,448 A | * | 3/1986 | Kambin ........................ 128/1 R |
| 4,657,017 A | * | 4/1987 | Sorochenko .................. 606/45 |
| 4,907,589 A | | 3/1990 | Cosman |
| 4,950,267 A | | 8/1990 | Ishihara et al. |
| 4,963,142 A | | 10/1990 | Loertscher |
| 4,966,144 A | | 10/1990 | Rochkind et al. |
| 5,061,266 A | | 10/1991 | Hakky |
| 5,084,043 A | | 1/1992 | Hertzmann et al. |
| 5,209,748 A | | 5/1993 | Daikuzono |
| 5,222,953 A | | 6/1993 | Dowlatshahi |
| 5,242,439 A | | 9/1993 | Larsen et al. |

(List continued on next page.)

FOREIGN PATENT DOCUMENTS

| | | |
|---|---|---|
| EP | 1059067 | 12/2000 |
| WO | WO 01/45579 A1 | 6/2001 |

OTHER PUBLICATIONS

Mary S. Sherman; The Nerves of Bone, The Journal of Bone and Joint Surgery, Apr. 1963, pp. 522–528, vol. 45–A, No. 3.

Michael H. Heggeness, et al., The Trabecular Anatomy of Thoracolumbar Vertebrae: Implications for Burst Fractures, Journal of Anatomy, 1997, pp. 309–312, vol. 191, Great Britain.

J. B. Martin, et al., Vertebroplasty: Clinical Experience and Follow–up Results, Bone, Aug. 1999, pp. 11S–15S, vol. 25, No. 2, Supplement.

H. Deramond, et al., Temperature Elevation Caused by Bone Cement Polymerization During Vertebroplasty, Bone, Aug. 1999, pp. 17S–21S, vol. 25, No. 2, Supplement.

*Primary Examiner*—Roy D. Gibson
(74) *Attorney, Agent, or Firm*—Anthony F. Matheny; Andrews Kurth LLP (57) ABSTRACT

The invention relates to surgical devices, and in particular, ablating probes for ablating, or severing, intraosseous nerves. The ablating probes are used to ablate or sever the pathway of intraosseous nerves after the ablating probe contacts, or is positioned in close proximity to, the intraosseous nerve. Access to the intraosseous nerve may be provided by the ablating probe or another instrument. The invention is also directed to a surgical system for ablating intraosseous nerves that comprises at least one nerve ablating device, e.g., the ablating probes of the invention, and at least one sleeve through which the ablating probe is passed to contact the intraosseous nerve, or the area in close proximity to the intraosseous nerve, thereby facilitating ablation of the intraosseous nerve. Methods of ablating intraosseous nerves are also disclosed.

44 Claims, 8 Drawing Sheets

U.S. PATENT DOCUMENTS

| | | | |
|---|---|---|---|
| 5,281,213 A | 1/1994 | Milder et al. | |
| 5,320,617 A | 6/1994 | Leach | |
| 5,350,377 A | 9/1994 | Winston et al. | |
| 5,368,031 A | 11/1994 | Cline et al. | |
| 5,433,739 A | 7/1995 | Sluijter et al. | |
| 5,437,661 A | 8/1995 | Rieser | |
| 5,486,170 A | 1/1996 | Winston et al. | |
| 5,571,147 A | 11/1996 | Sluijter et al. | |
| 5,697,927 A | 12/1997 | Imran et al. | |
| 5,700,262 A | 12/1997 | Acosta et al. | |
| 5,735,847 A | 4/1998 | Gough et al. | |
| 5,738,680 A | 4/1998 | Mueller et al. | |
| 5,746,737 A | 5/1998 | Saadat | |
| 5,849,011 A | 12/1998 | Jones et al. | |
| 5,941,876 A | 8/1999 | Nardella et al. | |
| 5,948,007 A | 9/1999 | Starkebaum et al. | |
| 5,948,008 A * | 9/1999 | Daikuzono | 607/89 |
| 5,983,141 A | 11/1999 | Sluijter et al. | |
| 6,007,533 A * | 12/1999 | Casscells et al. | 606/45 |
| 6,007,570 A | 12/1999 | Sharkey et al. | |
| 6,073,051 A | 6/2000 | Sharkey et al. | |
| 6,099,514 A | 8/2000 | Sharkey et al. | |
| 6,104,957 A | 8/2000 | Alo et al. | |
| 6,117,128 A | 9/2000 | Gregory | |
| 6,120,467 A | 9/2000 | Schallhorn | |
| 6,122,549 A | 9/2000 | Sharkey et al. | |
| 6,139,545 A | 10/2000 | Utley et al. | |
| 6,143,019 A | 11/2000 | Motamedi et al. | |
| 6,190,383 B1 * | 2/2001 | Schmaltz et al. | 606/41 |
| 6,193,715 B1 * | 2/2001 | Wrublewski et al. | 606/45 |
| 6,241,665 B1 | 6/2001 | Negus et al. | |
| 6,241,725 B1 | 6/2001 | Cosman | |
| 6,246,912 B1 | 6/2001 | Sluijter et al. | |
| 6,258,086 B1 * | 7/2001 | Ashley et al. | 606/41 |
| 6,259,952 B1 | 7/2001 | Sluijter et al. | |
| 6,264,650 B1 * | 7/2001 | Hovda et al. | 606/41 |
| 6,287,114 B1 | 9/2001 | Meller et al. | |
| 6,468,270 B1 * | 10/2002 | Hovda et al. | 606/41 |
| 6,478,793 B1 * | 11/2002 | Cosman et al. | 606/41 |

* cited by examiner

METHODS AND DEVICES FOR INTRAOSSEOUS NERVE ABLATION

RELATED APPLICATION

This application claims the benefit of U.S. Provisional Patent Application Serial No. 60/179,959, filed Feb. 3, 2000.

BACKGROUND OF THE INVENTION

1. Field of the Invention

This invention relates to surgical devices, and in particular, surgical systems for ablating intraosseous nerves. The invention also relates to methods for ablating intraosseous nerves.

2. Description of Related Art

Body pain may originate in muscles, organs, bones, or other areas of the body. One example of body pain is back pain, or pain associated with the spine. Back pain is a huge health problem worldwide and is the cause of much human suffering. Back pain is also a major cause for work-related disability benefits and compensation. Treatments for back pain vary widely, ranging from physical therapy, to pharmacological therapy and pain management, to surgical intervention.

Use of pharmaceuticals to treat back pain has at least three concerns. First, the patient may become dependent upon the pharmaceuticals. Second, the cost of the pharmaceuticals, usually over several years, may be extremely costly. Third, generally, the pain persists over many years.

Surgery also presents several concerns. First, most techniques involve fusing the vertebrae of the spine together and/or removing tissue from between the vertebrae. While surgery usually provides long-term relief, i.e., greater than one-year, surgical techniques require extensive recovery time and additional physical therapy for the patient.

While physical therapy does not present all of the concerns of surgery and many of the concerns with using pharmaceuticals, patients receive varying degrees of relief from pain. Additionally, physical therapy usually provides only short-term pain relief, i.e., one to two months, thereby extending treatment over several years, and thus increasing the cost of treatment. Moreover, many patients ultimately require surgery.

Accordingly, prior to the development of the present invention, there has been no surgical devices and surgical systems for ablating intraosseous nerves and methods of ablating intraosseous nerves, which: decreases the long-term cost for treatment for pain; decreases the use of pharmaceuticals; and provides long-term pain relief. Therefore, the art has sought a surgical device and surgical system for ablating intraosseous nerves and a method of ablating intraosseous nerves, which: decreases the long-term cost for treatment for pain; decreases the use of pharmaceuticals; and provides long-term pain relief. It is believed that the present invention will achieve these objectives and overcome the disadvantages of other surgical devices and surgical systems for ablating intraosseous nerves and methods of ablating intraosseous nerves in the field of the invention, but its results or effects are still dependent upon the skill and training of the operators and surgeons.

SUMMARY OF INVENTION

In accordance with the invention, the foregoing advantages have been achieved through the present ablating probe for ablating intraosseous nerves comprising: a shaft having a first end, a second end, and a length defined therebetween, wherein the second end of the shaft is adapted to be operatively associated with an electrical power source; and a tip disposed at the first end, the tip being formed from an electrically conductive material.

A further feature of the ablating probe for ablating intraosseous nerves is that the shaft may include at least one drill thread disposed along the shaft in proximity to the first end, and the second end may be adapted to be operatively associated with a drill. An additional feature of the ablating probe for ablating intraosseous nerves is that the shaft may include at least one handle. Another feature of the ablating probe for ablating intraosseous nerves is that the tip may be blunted. A further feature of the ablating probe for ablating intraosseous nerves is that the tip may be pointed. An additional feature of the ablating probe for ablating intraosseous nerves is that the shaft may be formed from electrically conductive material and the shaft may include an insulating layer disposed along a portion of the shaft. Another feature of the ablating probe for ablating intraosseous nerves is that the portion of the shaft having the insulating layer disposed thereon may include at least one drill thread disposed thereon in proximity to the first end, and the second end may be adapted to be operatively associated with a drill.

In accordance with the invention, the foregoing advantages have also been achieved through the present ablating probe for ablating intraosseous nerves comprising: a shaft having a first end, a second end, a length defined therebetween, and at least one cavity, wherein the second end of the shaft is adapted to be operatively associated with a fluid source; and a tip disposed at the first end.

A further feature of the ablating probe for ablating intraosseous nerves is that the shaft may include at least two cavities. Another feature of the ablating probe for ablating intraosseous nerves is that the tip may be blunted. An additional feature of the ablating probe for ablating intraosseous nerves is that the tip may be pointed. Still another feature of the ablating probe for ablating intraosseous nerves is that the shaft may include at least one handle.

In accordance with the invention, the foregoing advantages have also been achieved through the present intraosseous nerve ablation system comprising: at least one nerve ablation device; and at least one sleeve, wherein the at least one nerve ablation device or the at least one sleeve is adapted for creating a passageway in a bone, thereby providing access to the intraosseous nerve.

A further feature of intraosseous nerve ablation system is that the at least one nerve ablating device may be an ablating probe having a shaft, the shaft having a first end including a tip formed from an electrically conductive material, a second end adapted to be operatively associated with an electrical power source, and a length defined between the first end and the second end. Another feature of intraosseous nerve ablation system is that the at least one nerve ablating device may be an ablating probe having a shaft, the shaft having a first end, a second end adapted to be operatively associated with a fluid source, a length defined between the first end and the second end, and at least one cavity. An additional feature of intraosseous nerve ablation system is that the at least one nerve ablating device may be a laser. Still another feature of intraosseous nerve ablation system is that the intraosseous nerve ablation system may include two sleeves. A further feature of intraosseous nerve ablation system is that the at least one sleeve may include a first end having an edge surface, a second end, a length defined between the first end and the second end, and a cavity. Another feature of intraosseous nerve ablation system is that the edge surface may be serrated. An additional feature of intraosseous nerve ablation system is that the edge surface may be pointed.

In accordance with the invention, the foregoing advantages have also been achieved through the present method of ablating an intraosseous nerve comprising the steps of: providing a nerve disposed within a bone and at least one ablating device; creating a passageway in the bone, thereby providing access to the intraosseous nerve; inserting the at least one ablating device into the passageway until the at least one ablating device contacts, or is in close proximity to, the intraosseous nerve; and activating the at least one ablating device, thereby ablating the intraosseous nerve.

A further feature of the method of ablating an intraosseous nerve is that the at least one ablating device may be activated by transmitting electricity through the nerve ablation device. Another feature of the method of ablating an intraosseous nerve is that the at least one ablating device may be activated by transmitting a fluid into, or through, the nerve ablation device. An additional feature of the method of ablating an intraosseous nerve is that the nerve ablation device may be an ablating probe and the passageway may be created in the bone by the ablating probe. Still another feature of the method of ablating an intraosseous nerve is that the passageway may be created in the bone by a sleeve having at least one cavity and the nerve ablation device may be inserted into the cavity of the sleeve and through the passageway until the nerve ablation device contacts, or is in close proximity to, the intraosseous nerve. A further feature of the method of ablating an intraosseous nerve is that the intraosseous nerve may be a basivertebral nerve having an exit point. Another feature of the method of ablating an intraosseous nerve is that the basivertebral nerve may be ablated at, or in close proximity to, the exit point.

The surgical devices and surgical systems for ablating intraosseous nerves and methods of ablating intraosseous nerves have the advantages of: decreasing the long-term cost for treatment for pain; decreasing the use of pharmaceuticals; and providing long-term pain relief. As mentioned above, it is believed that the present invention will achieve these objectives and overcome the disadvantages of other surgical devices and surgical systems and methods in the field of the invention, but its results or effects are still dependent upon the skill and training of the operators and surgeons.

BRIEF DESCRIPTION OF DRAWINGS

FIG. 11b is a side view of the vertebra shown in FIG. 11a.

FIG. 12b is a side view of the vertebra shown in FIG. 12a.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION AND SPECIFIC EMBODIMENTS

The present invention is directed to surgical devices and surgical systems for intraosseous nerve ablation as well as methods of ablating intraosseous nerves. While the description of surgical devices, surgical systems, and methods of ablating intraosseous nerves will be directed to intraosseous nerves of the vertebrae, and in particular, the basivertebral nerves located within the vertebrae, it is to be understood that the surgical devices, surgical systems, and methods of ablating intraosseous nerves of the invention may be used, or performed, in connection with any intraosseous nerve, e.g., nerves located within the pelvis, the femur, the fibula, the tibia, humerus, ulna, radius, or any other bone.

The surgical devices for ablating intraosseous nerves are broadly referred to herein as nerve ablation devices 10. Nerve ablation devices 10 are any instrument or device that is capable, when activated, of severing, or ablating, an intraosseous neural pathway. Examples of nerve ablation devices 10 include, but are not limited to, the ablating probes 20 described in greater detail below as well as laser devices and tubes used in connection with fluids and laser devices.

"Activated" means functioning as intended by the design of the specific nerve ablation device 10. For example, the electricity transmitting nerve ablation devices discussed in greater detail below are "activated" when electricity is passed through the nerve ablation device 10. Further, fluid nerve ablation devices and laser nerve ablation devices, also discussed in greater detail below, are "activated" when fluid is transmitted into, or through the nerve ablation device, or laser energy is transmitted from the laser, respectively.

Certain embodiments of ablating probes 20 are configured to transmit electrical currents into bones, e.g., the vertebral body, to ablate the nerves located therein ("intraosseous nerves"). Other embodiments of the ablating probes employ means for thermal ablation, while in another embodiment the ablating probe is adapted to carry medications and/or chemical substances, including chemotherapy and radioactive substances, to the site of the intraosseous nerves for subsequent nerve ablation by these substances.

In other embodiments of the present invention, surgical systems, or intraosseous nerve ablation systems, include at least one nerve ablation device and at least one sleeve that is adapted to facilitate alignment of the nerve ablation device with the passageway for accessing the intraosseous nerve. The sleeve may also facilitate cutting, or penetrating, the bone to create a bore, or passageway, through which the nerve ablation device may be inserted for subsequent nerve ablation. The sleeve may also be used for engagement of the nerve abation device with the bone to guide the nerve ablation device during cutting, drilling, or penetrating the bone and/or the intraosseous nerve ablation process.

Proper positioning of the ablating device, including positioning of the ablating probe, as well as proper formation of the passageway in the bone for providing access to the intraosseous nerve, may be facilitated by computer tomography (CT), fluoroscopy, or any other device or instrument known to persons skilled in the art.

The present invention is further directed to methods of ablating nerves contained within the bone, and in particular, to methods of ablating the basivertebral nerves recently discovered by the inventor that are located within human vertebral bodies. The basivertebral nerves have been found to stain positively in the presence of Substance P which is indicative of the ability of the basivertebral nerves to transmit the sensation of pain to the brain. Substance P is an antigen the presence of which is associated with pain transmission by nerves. In specific embodiments of the methods of ablating intraosseous nerves, the basivertebral nerves are ablated through different passageways created in the vertebral body by the surgeon for the purpose of intraosseous nerve ablation.

Figure 1:
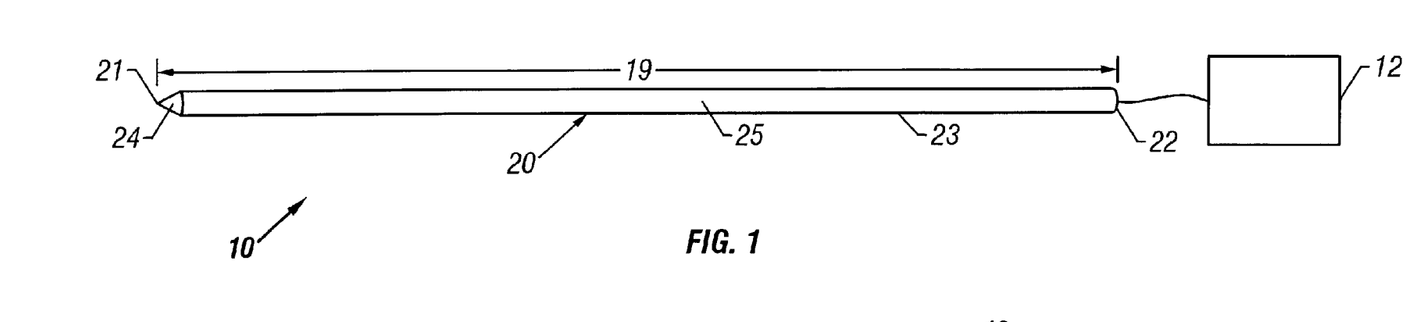
FIG. 1 is a side view of a specific embodiment of the ablating probe of the present invention.
Figure 2:
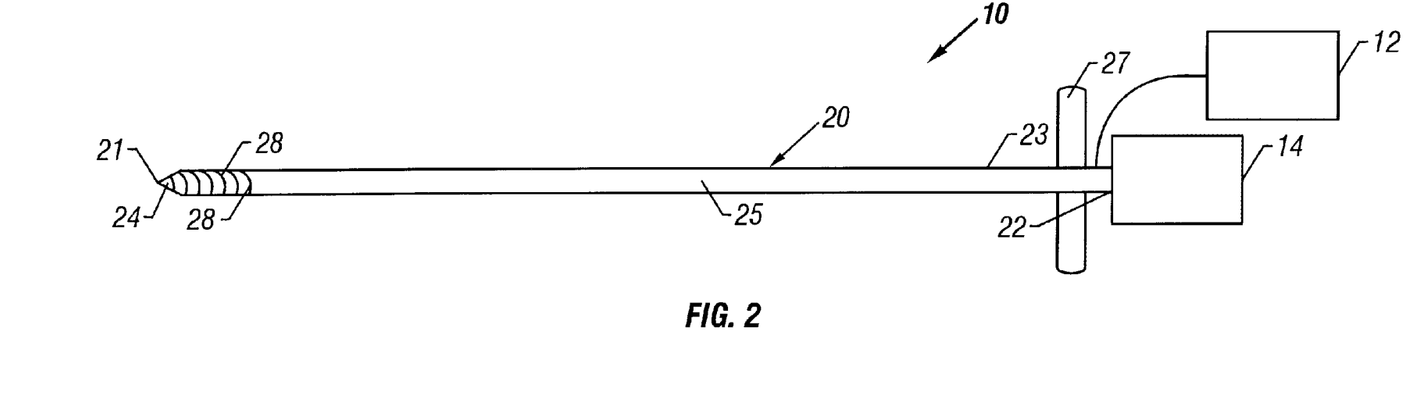
FIG. 2 is side view of another specific embodiment of the ablating probe of the present invention.
Figure 3A:
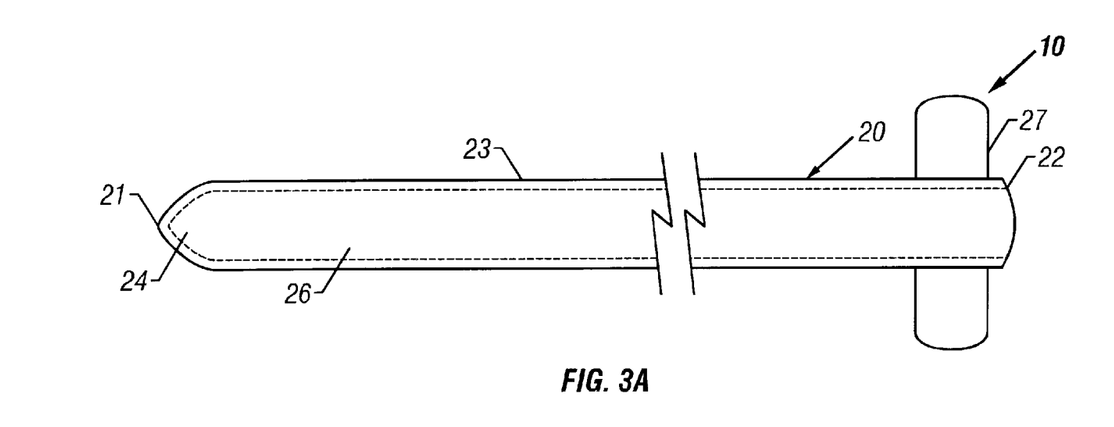
FIG. 3a is a side view of still another specific embodiment of the ablating probe of the present invention.
Figure 3B:
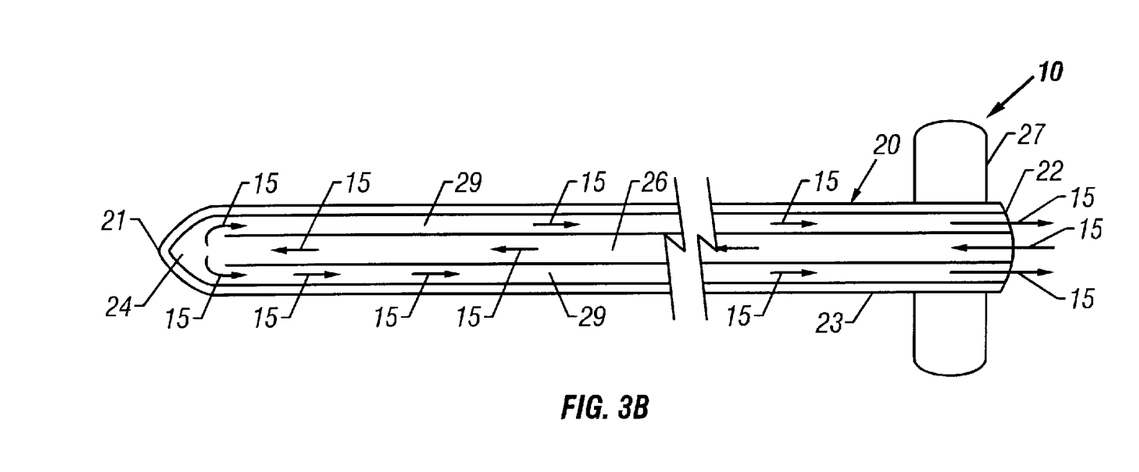
FIG. 3b is a side view of yet another specific embodiment of the ablating probe of the present invention.

Referring now to FIGS. 1–3b, in one aspect, the present invention is directed to ablating probes 20 having shaft 23. Shaft 23 includes first end 21, second end 22, and length 19 defined therebetween. Length 19 may be straight or curved. As shown in FIGS. 1–3, length 19 is straight. First end 21 includes tip 24. Tip 24 may be pointed, as shown in FIGS. 1–2, or blunt as shown in FIG. 3. In the embodiments in which tip 24 is pointed tip 24 may be use to facilitate penetration of the ablating probe 20 through the bone to access the intraosseous nerve. Second end 22 may include a handle 27 to permit the surgeon to steady ablating probe 20 during use.

In one specific embodiment shown in FIG. 2, ablating probe 20 includes drill threads 28. Drill threads 28 assist ablating probe 20 to create a passageway in the bone to access the intraosseous nerve. In this embodiment, drill 14 is preferably used to facilitate creation of the passageway. Accordingly, second end 22 of ablating probe 20 is preferably configured such that second end 22 may be operatively associated with drill 14. Configuration of second end 22 to be operatively associated with drill 14 is readily known to persons of ordinary skill in the art.

Still referring to FIGS. 1–2, first end 21 of ablating probe 20 is formed from an electrically conductive material. The electrically conductive material may be any electrically conductive material known to persons of ordinary skill in art. Exemplary electrically conductive materials include steel, titanium, and other metals and metal alloys commonly used in the medical device/instrumentation arts. Shaft 23 may also be formed of an electrically conductive material. In this embodiment, shaft 23 preferably includes an insulating layer 25 that is not electrically conductive. Insulating layer 25 may be formed out of any non-electrically conductive material known to persons of ordinary skill in the art. Preferred non-electrically conductive materials include plastic, rubber, and ceramic.

In one embodiment, e.g., as shown in FIG. 1, the passageway is formed by a boring device, e.g., a drill. After the passageway is formed in the bone, thereby providing access to the intraosseous nerve to be ablated, first end 21 of ablating probe 20 is inserted through the passageway in the bone until tip 24 contacts, or is in close proximity to, the intraosseous nerve. "Close proximity to" with regard to the location of nerve ablation device 10 relative to the intraosseous nerve means located at a position such that the intraosseous nerve is ablated upon activation of nerve ablation device 10. After ablating probe 20 is positioned in this manner, ablating probe 20 is activated, i.e., an electrical current from an electric power source 12 operatively associated with second end 22 of ablating probe 20 is transmitted from an electric power source 12, through shaft 23, and through tip 24 to ablate the intraosseous nerve. The electrical current raises the temperature of tip 24 such that the intraosseous nerve is ablated by the heat generated by the electrical current passing through tip 24.

In another embodiment, drill threads 28 (FIG. 2) may be located along shaft 23 or along the insulating material 25. As shown in FIG. 2, drill threads 28 are disposed along shaft 23 in proximity to first end 21. "Proximity" with regard to the location of drill threads 28 means the portion of length 19 closer to first end 21 than to second end 22. In this embodiment, second end 22 of shaft 23 is preferably adapted to be operatively associated with drill 14. Tip 24 having drill treads 28 disposed along shaft 23 proximate to tip 24 is placed onto the bone. Drill 14 may then be powered to drive tip 24, and thus, shaft 23, through the bone to create a passageway thereby providing access to the intraosseous nerve. Electrical current may then be transmitted through tip 24 to ablate the intraosseous nerves in the same manner as previously described.

Referring now to FIGS. 3a and 3b, in another specific embodiment, ablating probe 20 includes at least one cavity 26 for holding fluids or other substances within, or passing fluids or other substances through, ablating probe 20. As shown in FIG. 3a, ablating probe 20 includes one cavity 26 that may be filled with a fluid or other substance for ablating the intraosseous nerve. As shown in FIG. 3b, ablating probe 20 includes two cavities 26, 29 thereby permitting fluid or other substance to be circulated through ablating probe 20. Drill threads 28 (as shown in FIG. 2) may be disposed along shaft 23 in these embodiments in the same manner as described above for use in the same manner as described above.

In the embodiments shown in FIGS. 3a and 3b, after a passageway is formed in the bone providing access to the intraosseous nerve, first end 21 of ablating probe 20 is inserted through the passageway in the bone until tip 24 contacts, or is in close proximity to, the intraosseous nerve. After ablating probe 20 is positioned in this manner, the intraosseous nerve may be ablated by use of a fluid. For example, intraosseous nerve may be ablated by localized freezing such as through the use of fluids such as liquid nitrogen, liquid air, or liquid nitrous oxide contained within cavity 26 (FIG. 3a), or circulating through cavities 26 and 29 in the directions of arrows 15 (FIG. 3b), of ablating probe 20. In this embodiment, second end 22 is preferably adapted to be operatively associated with a fluid reservoir (not shown), e.g., a syringe, a fluid pump, etc. to facilitate transmission of the fluid into cavity 26, or through cavities 26, 29.

Alternatively, ablating probe 20 shown in FIGS. 3a and 3b may include a sharp-pointed tip 24, capable of forming the passageway. Drill threads 28 may also be disposed along shaft 23 in proximity to first end 21, and second end 22 may be adapted to be operatively associated with a boring device, e.g., drill 14, as discussed above to facilitate the creation of the passageway. In this embodiment, ablating probe 20 penetrates the bone to a predetermined position, i.e., in contact with, or in close proximity to, the intraosseous nerve to be ablated. Intraosseous nerve may then be ablated in the same manner as discussed in the preceding paragraph.

Ablating probe 20 may have any length, shape, or diameter desired or required to provide access to the intraosseous nerve thereby facilitating effective ablation of the intraosseous nerve. Therefore, the size of the intraosseous nerve to be ablated, the size of the passageway in the bone for accessing the intraosseous nerve, and the location of the bone, and thus the intraosseous nerve, are factors that assist in determining the desired size and shape of ablating probe 10. In a preferred embodiment, ablating probe 20 is cylindrically-shaped having a straight length with a diameter in the range from about 1 mm to about 5 mm and a length in the range from about 25 cm to about 35 cm.

Figure 4:
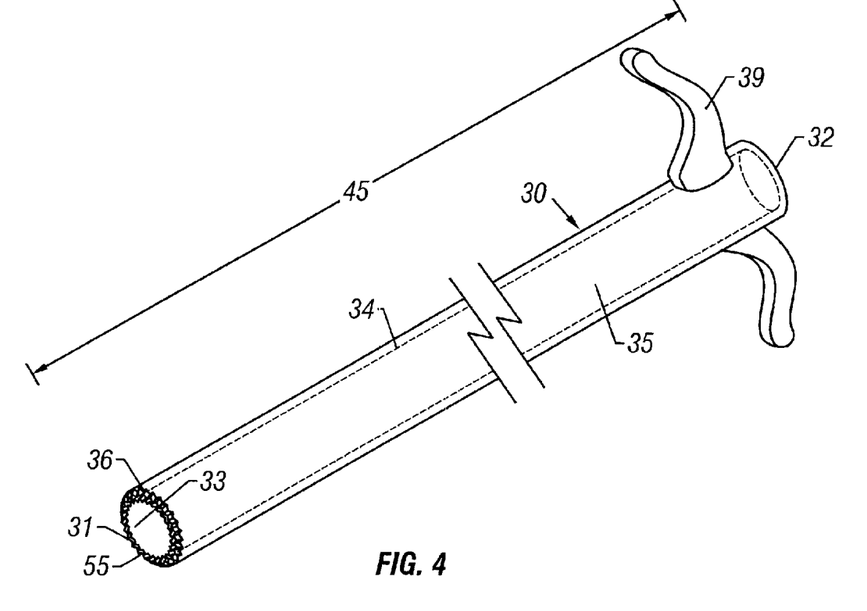
FIG. 4 is a perspective view of a specific embodiment of a sleeve that may be employed as part of a specific embodiment of the intraosseous nerve ablation system of the present invention.
Figure 5:
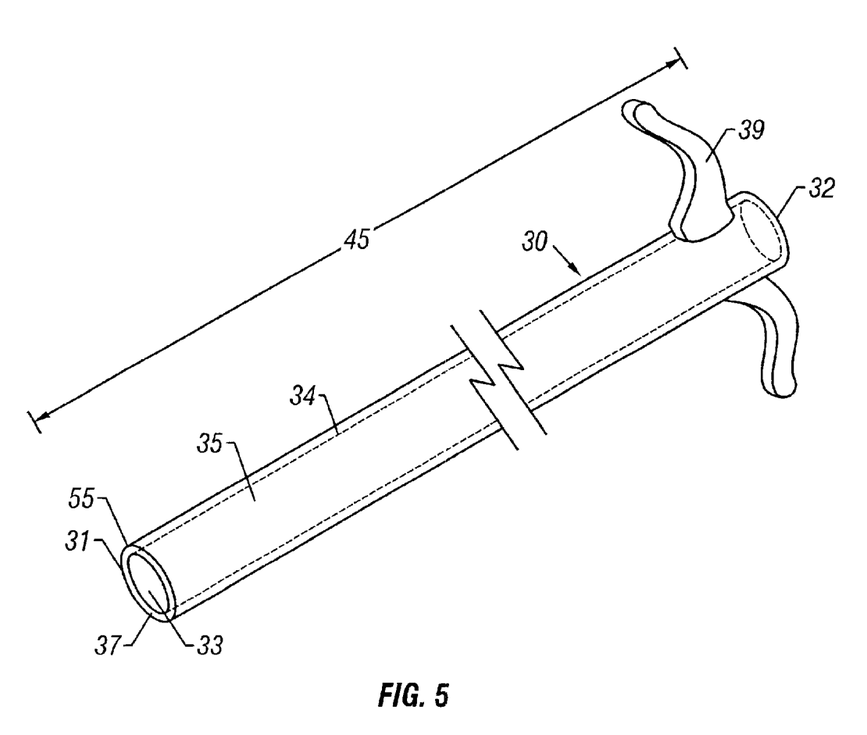
FIG. 5 is a perspective view of another specific embodiment of a sleeve that may be employed as part of another specific embodiment of the intraosseous nerve ablation system of the present invention.
Figure 6:
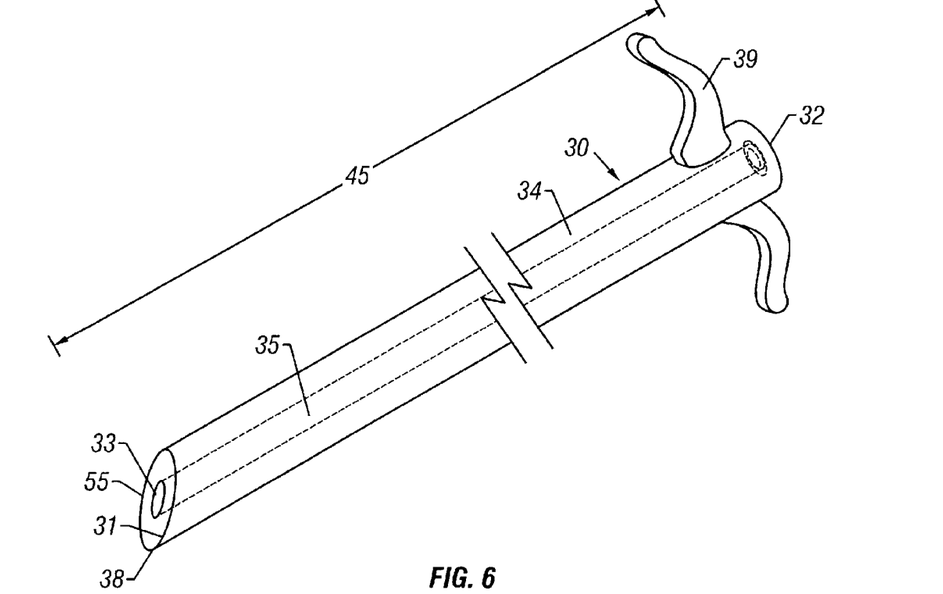
FIG. 6 is a perspective view of still another specific embodiment of a sleeve that may be employed as part of another specific embodiment of the intraosseous nerve ablation system of the present invention.

Referring now to FIGS. 4–6, the present invention is also directed to surgical system, or intraosseous nerve ablation system, 50 comprising at least on nerve ablation device 10 and at least one cannula or sleeve 30. Sleeve 30 serves as a guide for nerve ablation device 10 for more accurate penetration of the bone. Further, sleeve 30 protects adjacent soft tissues from injury as nerve ablation device 10 creates the passageway through the bone and/or ablates the intraosseous nerve. Sleeve 30 includes first end 31, second end 32, a length 45 defined between first end 31 and second end 32, inner wall surface 33, outer wall surface 34, and cavity 35. Length 45 may be straight or curved. As shown in FIGS. 4–6, length 45 is straight. Sleeve 30 may also include handle 39 to permit the surgeon to steady the sleeve 30 during use.

First end 31 includes edge surface 55 which may be serrated 36 (FIG. 4), smooth 37 (FIG. 5), or pointed 38 (FIG. 6). Serrated edge 36 (FIG. 4) permits sleeve 30 to be steadied against the bone, i.e., prevent slippage, and may be used to create a passageway in the bone for passage of the ablating probe 20. Pointed edge 38 (FIG. 6) is preferably sharp and may be used to steady sleeve 30 against the bone by the surgeon during use. Pointed edge 38 may also be used to create a passageway in the bone by circular cutting, drilling motion, or direct puncture of pointed edge 38 through the bone to access the intraosseous nerve. In the embodiment in which sleeve 30 is used to penetrate the bone, i.e., create the passageway to provide access to the intraosseous nerve, the nerve ablation device 10 may then be inserted through cavity 35 to ablate the intraosseous nerve as described in greater detail above.

Sleeve 30 may have any length, shape, or diameter desired or required to provide access to the intraosseous nerve thereby facilitating effective ablation of the intraosseous nerve. Therefore, the size of the intraosseous nerve to be ablated, the size of the passageway in the bone for accessing the intraosseous nerve, and the location of the bone, and thus the intraosseous nerve, are factors that assist in determining the desired size and shape of sleeve 30. In a preferred embodiment, sleeve 30 is cylindrically-shaped having a diameter in the range from about 1 mm to about 5 mm and a straight length in the range from about 15 cm to about 35 cm.

Figure 7:
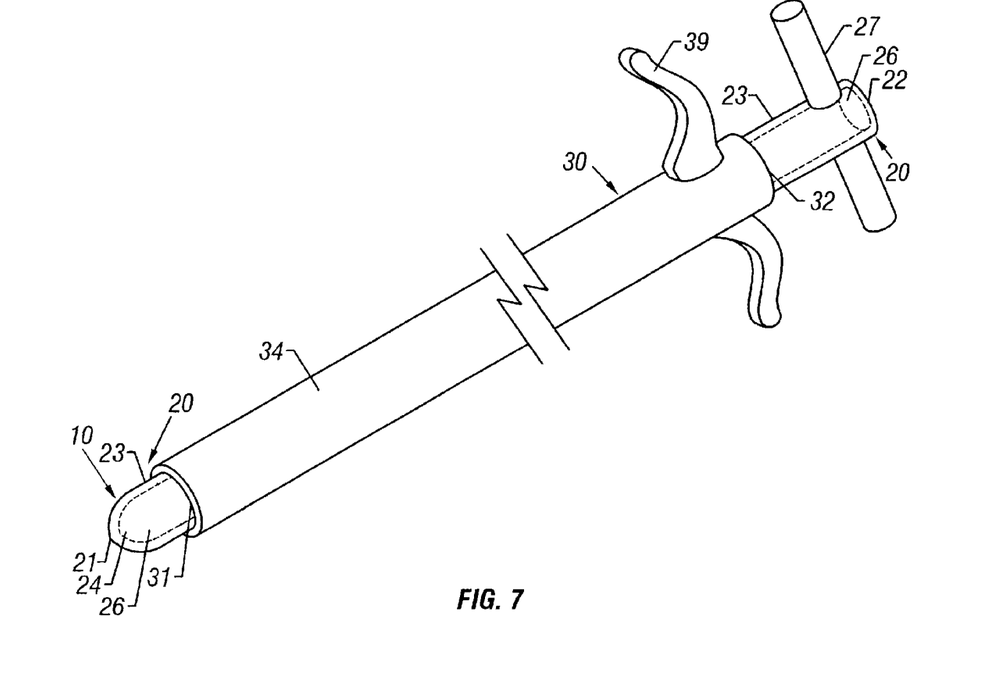
FIG. 7 is side view of the ablating probe shown in FIG. 3a and the sleeve shown in FIG. 5 which are a specific embodiment of the intraosseous nerve ablation system of the present invention.
Figure 8:
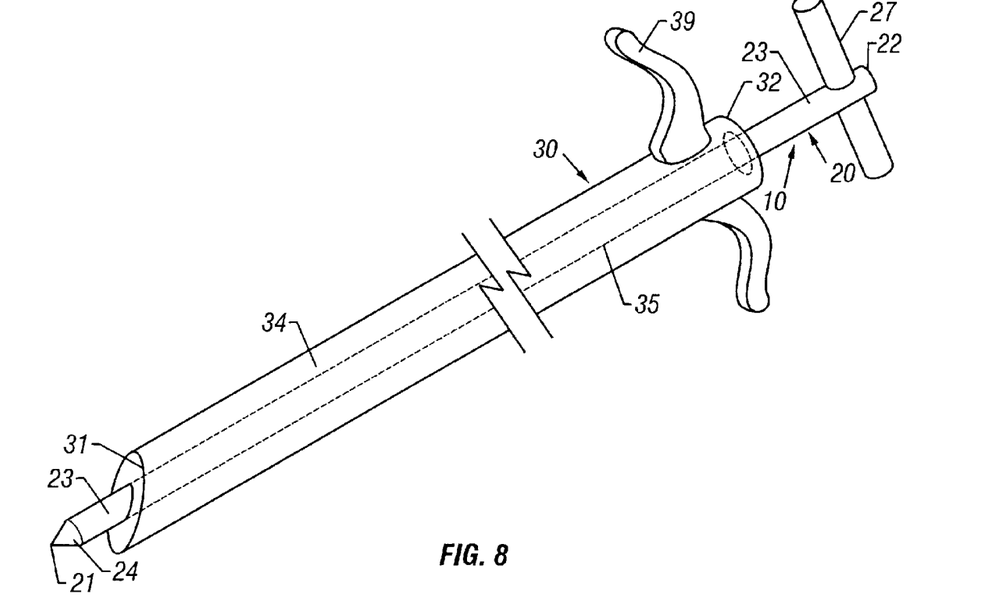
FIG. 8 is a perspective view the ablating probe shown in FIG. 1 and the sleeve shown in FIG. 6 which are another specific embodiment of the intraosseous nerve ablation system of the present invention.
Figure 9:
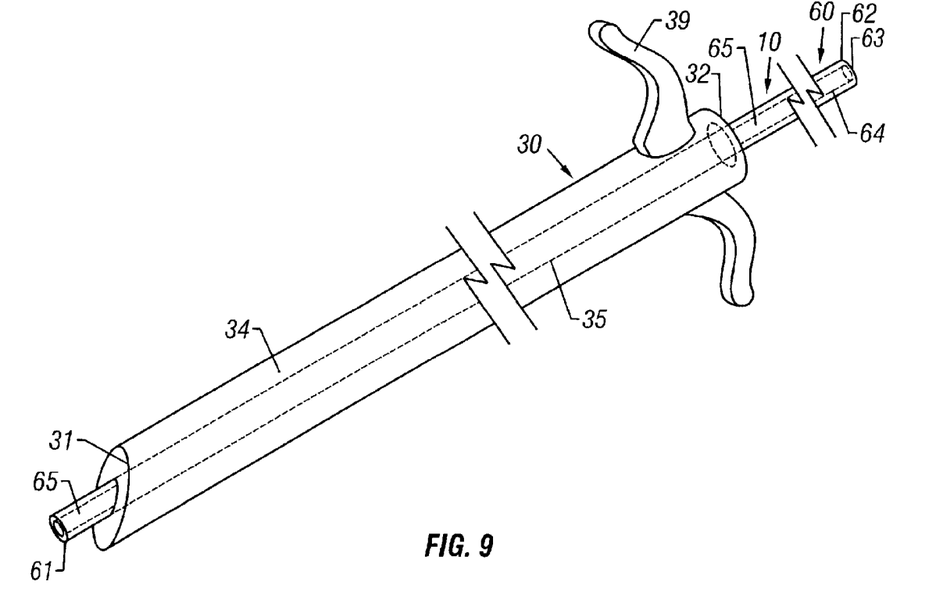
FIG. 9 is a perspective view of still another specific embodiment of the intraosseous nerve ablation system of the present invention.

Referring now to FIGS. 7–9, in another aspect, the present invention is directed to an intraosseous nerve ablation system 50 comprising at least one nerve ablation device 10 and at least one sleeve 30. FIG. 7 shows one specific intraosseous nerve ablation system 50 of the present invention comprising ablating probe 20 shown in FIG. 3 and sleeve 30 shown in FIG. 5. FIG. 8 shows another specific intraosseous nerve ablation system 50 of the present invention comprising ablating probe 20 shown in FIG. 1 and sleeve 30 shown in FIG. 6. In both of these embodiments, ablating probe 20 is shown passing through second end 32, into cavity 35, and out of first end 31 of sleeve 30.

Alternatively, as shown in FIG. 9, in another specific embodiment of the invention, the intraosseous nerve ablation system 50 includes a tube 60 as nerve ablation device 10 and sleeve 30 shown in FIG. 6. Tube 60 is disposed within cavity 35 of sleeve 30 by passing tube 60 through second end 32, into cavity 35, and out of first end 31 of sleeve 30.

Tube 60 includes first end 61, second end 62, inner wall surface 63, outer wall surface 64, and cavity 65. In this embodiment, tube 60 is adapted to transmit various medications, pharmaceuticals, or other chemical substances, such as alcohols, acids, and other solvents or fluids, through cavity 65 and into the bone to ablate the intraosseous nerve. Second end 62 may be in communication with a fluid source (not shown), e.g., a syringe, containing the fluid or other substance used to ablate the intraosseous nerve. The fluid may then be in transmitted through cavity 65 in the direction from second end 62 of tube 60 to first end 61 of tube 60 to ablate the intraosseous nerve.

Figure 10:
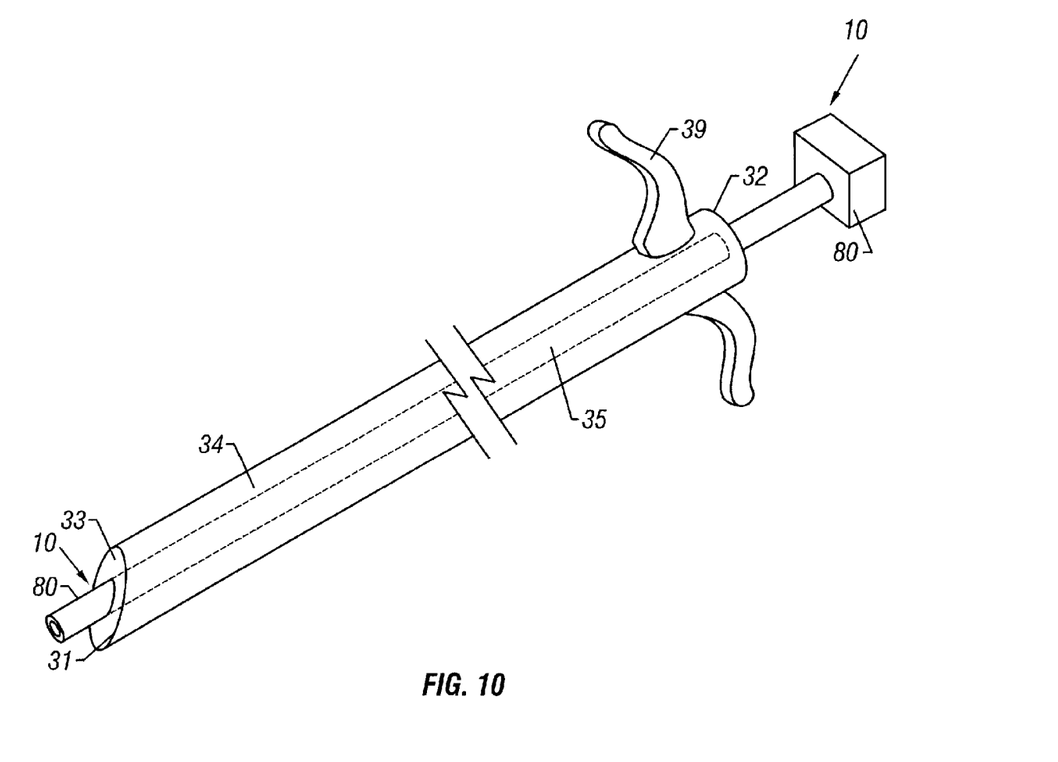
FIG. 10 is a perspective view of yet another specific embodiment of the intraosseous nerve ablation system of the present invention.

In another specific embodiment shown in FIG. 10, a laser 80, such as a fiber optic laser, is nerve ablation device 10 that is included as part of the intraosseous nerve ablation system 50. In this embodiment, laser 80 may be disposed within cavity 35 of sleeve 30 as shown in FIG. 10, or, alternatively, within cavity 65 of tube 60 such that laser energy may be directed out of first end 31 of sleeve 30, or first end 61 of tube 60, to ablate the intraosseous nerve. Various lasers 80 are known to persons skilled in the art who can readily determine the appropriate laser 80 to be used to ablate the intraosseous nerves.

In still another specific embodiment, the intraosseous nerve ablation system 50 may include at least one nerve ablation device 10, e.g., one or more of the ablating probes shown in FIGS. 1–3b, tube 60, or laser 80, and at least two sleeves 30. For example, intraosseous nerve ablation system 50 may include first sleeve 30, e.g., sleeve 30 shown in FIG. 4 or FIG. 5, and second sleeve 30, e.g., sleeve 30 shown in FIG. 6. In this embodiment, nerve ablation device 10 may be disposed within cavity 35 of second sleeve 30 as shown in FIG. 8. Second sleeve 30 and ablating probe 20 shown in FIG. 8 may then be disposed within cavity 35 of first sleeve 30 (FIG. 4 or FIG. 5). In this embodiment, first sleeve 30 shown in FIG. 4 or FIG. 5 steadies the surgical system 50 against the bone and second sleeve 30 shown in FIG. 6 facilitates the formation of the passageway in the bone as discussed above. After the passageway is formed, nerve ablation device 10 may then contact, or be placed in close proximity to, the intraosseous nerve, thereby permitting nerve ablation device 10 to ablate the intraosseous nerve.

The surgical devices and surgical systems described above may be use to ablate intraosseous nerves, and in particular basivertebral nerves. The inventor of the present invention has discovered the existence of substantial intraosseous nerve branches within human vertebral bodies ("basivertebral nerves") having at least one exit point. The exit point is the location along the basivertebral nerve where the basivertebral nerve exits the vertebrae. Preferably, the basivertebral nerves are ablated at, or in close proximity to, the exit point. It is understood that all intraosseous nerves include an exit point and that all of the intraosseous nerves are preferably ablated at, or in close proximity to, the exit point of the intraosseous nerves.

Moreover, after extensive study, the inventor further discovered that the basivertebral nerve tissues stained positively for Substance P, thus indicating that the basivertebral nerves are capable of transmitting pain. Table I below lists the results of Substance P staining of six cadaveric human vertebrae. The basivertebral nerves believed to have pain-transmitting properties were stained per this method. The symbol "+" indicates intensity of staining.

Staining for S100 proteins was also performed as a positive control. S100 proteins are found in astrocytes and Schwann's cells of nerves. Therefore, positive staining for S100 protein confirms the presence of neural tissue.

TABLE I

| Specimen Number | S100 staining | Substance P staining |
| --- | --- | --- |
| 1 | ++ | ++++ |
| 2 | + | ++++ |
| 3 | + | ++++ |
| 4 | ++ | ++++ |
| 5 | ++ | ++++ |
| 6 | ++ | ++++ |

As illustrated in TABLE I, a high positive response to the Substance P staining was observed. Because the basivertebral nerves exhibiting positive response to Substance P staining transmit pain, ablating the basivertebral nerves, preferably with the surgical devices, surgical systems, and methods described herein, pain transmission is believed to be diminished.

As shown in FIGS. 11a, 11b, 12a, 12b, a vertebrae 200 includes the vertebral body 201, the vertical arch comprising the lamina 203 and the pedicle or root 204, the transverse process 205, the spinous process or spine 206, the inferior articular process 207, the superior articular process 208, the vertebral foramen 209, the superior vertebral notch 210, and the inferior vertebral notch 211. Basivertebral nerves 100 are disposed within the vertebral body 201. Exit point 212 is the location along basivertebral nerve 100 where basivertebral nerve 100 exits the vertebral body 201.

It is contemplated that access to vertebrae 200 for subsequent intraosseous nerve ablation may be achieved in at least two ways. In one approach, the patient's skin is penetrated with a surgical instrument which is then used to access the desired basivertebral nerves, i.e., percutaneously. A second approach is to ablate the intraosseous nerves during a surgical repair of the spine, wherein the patient's spine, or a portion thereof, is fully exposed for the primary surgery (e.g., vertebral fracture repair, spinal fixation, tumor removal, etc.). The basivertebral nerves may then be ablated as a prophylactic measure against subsequent post-surgical back pain. It is noted that intraosseous nerve ablation may occur prior to the primary spinal surgery if desired by the surgeon.

Regardless of whether the basivertebral nerve ablation is performed percutaneously or as a secondary procedure during a conventional spinal surgical repair as discussed in the preceding paragraph, the following discussion is directed to various surgical methods of the present invention for accessing basivertebral nerves. While the following description is limited to three different approaches for accessing the basivertebral nerves, it is to be understood that alternative approaches may be taken by the surgeon depending upon the clinical setting. Additionally, as discussed above, while the methods of the invention will be discussed with reference to the basivertebral nerves, it is to be understood that the methods of the invention may be used to ablate intraosseous nerves other than basivertebral nerves.

Figure 11A:
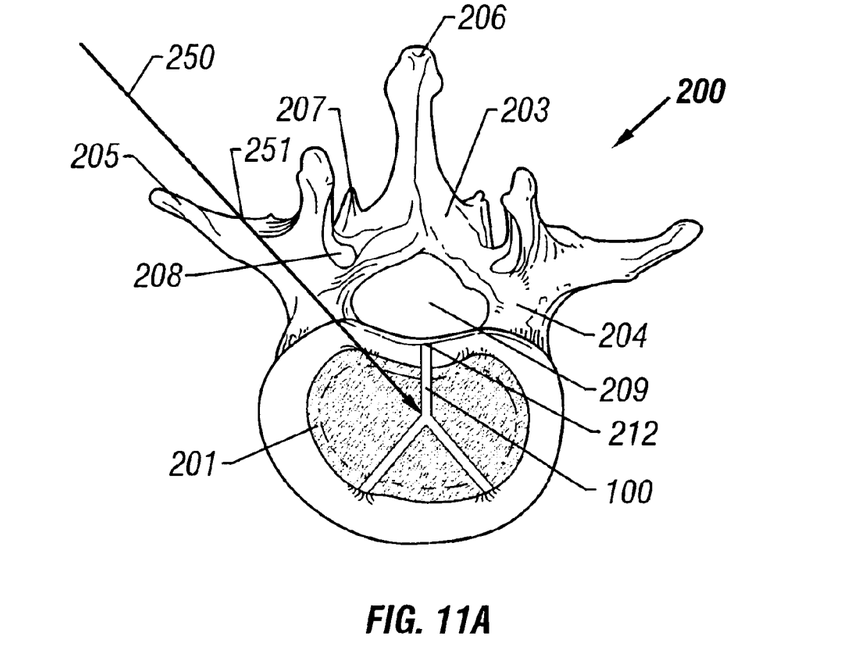
FIG. 11a is a top view of a vertebra illustrating the transpedicular approach for accessing the basivertebral nerve within the vertebral body.
Figure 11B:
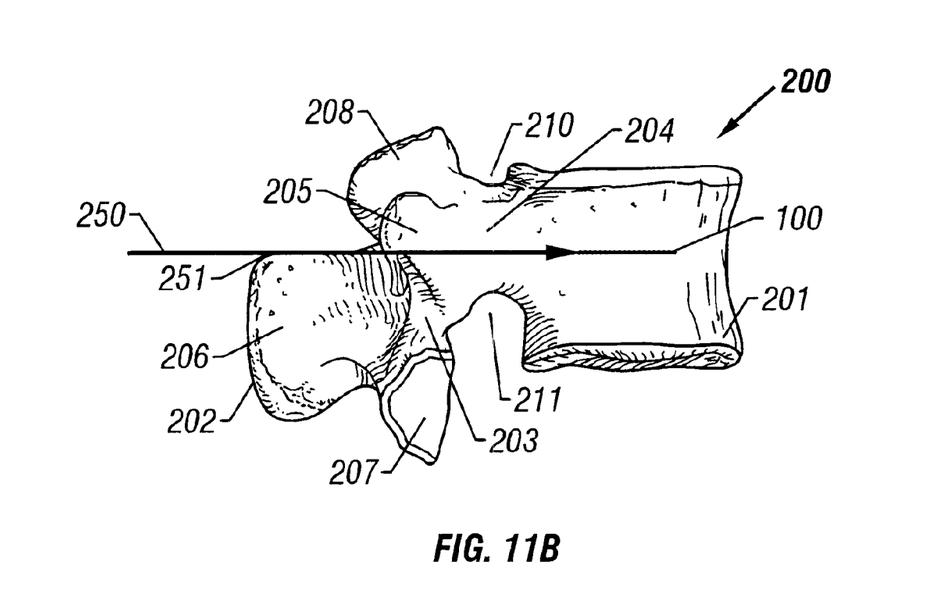

Referring now to FIGS. 11a–11b, the transpedicular approach for penetrating the vertebral cortex to access the basivertebral nerve 100 is shown. A passageway (not shown) is created starting at the point of entry 251 in the direction of penetration (arrow 250). The passageway is created along arrow 250 through the transverse process 205, the pedicle 204, and ultimately, the vertebral body 201 until the passageway contacts, or is in close proximity to, the basivertebral nerve 100 (located at the tip of arrow 250).

Figure 12A:
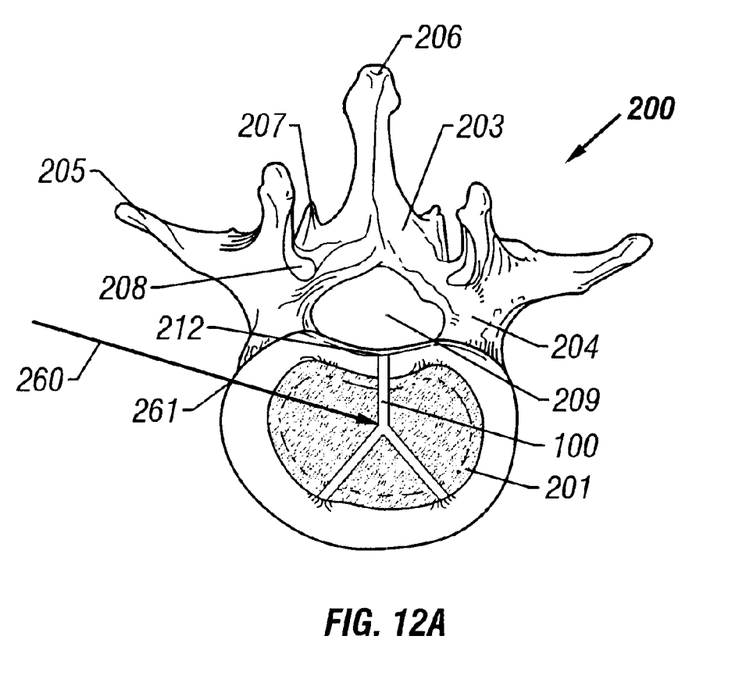
FIG. 12a is a top view of a vertebra illustrating the postereolateral approach for accessing the basivertebral nerve within the vertebral body.
Figure 12B:
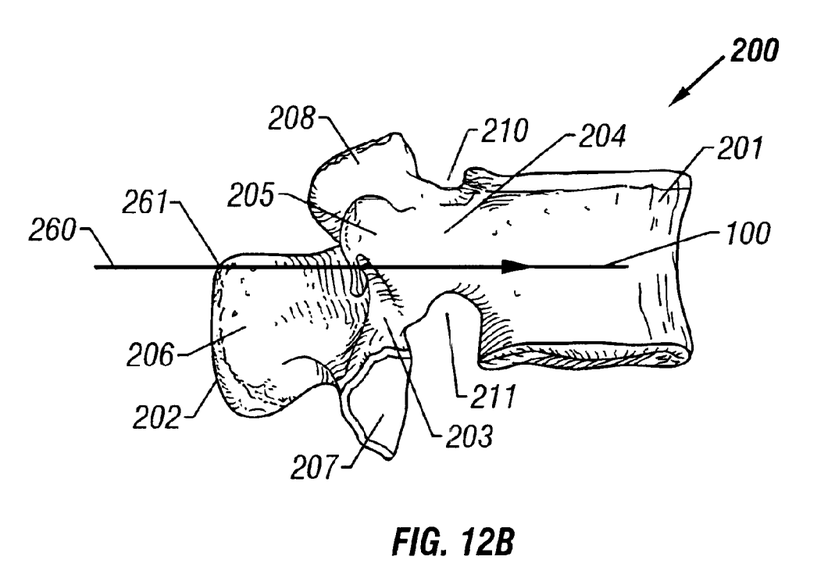

Referring now to FIGS. 12a–12b, the postereolateral approach for penetrating the vertebral cortex to access the basivertebral nerve 100 is shown. In this embodiment, a passageway (not shown) is create at the point of entry 261 in the direction of penetration, i.e., arrow 260. The passageway is created along arrow 260 through the posterior end 202 of the vertebral body 201 beneath the transverse process 205 until the passageway contacts, or is in close proximity to, the basivertebral nerve 100 (located at the tip of arrow 260).

As discussed above, the passageway may be created using ablating probe 20, sleeve 30, or with any other boring device, e.g., drill 14 with drill bit (not shown), by boring through the vertebrae 200 at the point of entry, e.g., 251 (FIGS. 11a–11b) and 261 (FIGS. 12a–12b). In the embodiment in which the passageway is created using boring device, e.g., drill 14 and drill bit, the boring device is removed from the passageway in the bone and nerve ablation device 10, e.g., ablating probe 20, laser 80, or tube 60, is inserted into the passageway and the basivertebral nerve 100 is ablated using the nerve ablation device 10 as discussed above.

Alternatively, the passageway may be created by ablating probe 20 which will then be in place to ablate the basivertebral nerve 100 as discussed above, e.g., using electrical current, chemicals, fluids, etc.

In another embodiment, at least one sleeve 30 may be inserted into the passageway, or placed in contact with the lateral cortex of the vertebra, near the transverse process 205, to facilitate creation of the passageway, and thus provide access to basivertebral nerve 100. In this embodiment, sleeve 30 is placed in contact with the vertebrae 200 at the point of entry 251, 261, and used to create a passageway in the bone along arrow 250, 260. Ablating probe 20, laser 80, or tube 60 may then be disposed within cavity 35 of sleeve 30, and thus, be aligned along arrow 250, 260, to access and ablate the basivertebral nerve as discussed above.

When sleeve 30 is used to create the passageway, either alone or in combination with a second sleeve 30, sleeve 30 is aligned over entry point 251, 261 prior to cutting or penetrating the bone. A passageway is created deep enough to allow penetration of the sleeve 30 through the bone such that first end 31 of sleeve 30 contacts, or is positioned in close proximity to, basivertebral nerve 100 for subsequent ablation as discussed above.

In still another approach, the basivertebral nerve 100 may be accessed without creating a passageway through the vertebrae 200 as shown in FIGS. 11*a*, 11*b*, 12*a*, 12*b*. Instead, the basivertebral nerve 100 may be accessed through the vertebral foramen 209.

In one specific embodiment of the method of ablating an intraosseous nerve, a ablating probe 20 is placed in contact with a bone surface. Ablating probe 20 penetrates the bone surface thereby creating a passageway in the bone to a predetermined depth. Ablating probe 20 may penetrate the bone surface by direct puncture or by drilling ablating probe 20 into the bone surface using drill 14. Ablating probe 20 is then activated thereby ablating the intraosseous nerve. Ablating probe 20 may be activated as described above, e.g., by use of an electrical current, a fluid, etc. Further, sleeve 30 may be placed in contact with the bone surface to facilitate alignment of the ablating probe 20 with the bone surface during formation of the passageway, as well as during ablation of the intraosseous nerve.

In another specific embodiment, the passageway is formed using a boring device, e.g., a drill and drill bit. Further, sleeve 30 may be placed in contact with the bone surface to facilitate alignment of the boring device with the bone surface during formation of the passageway. After the drill bit penetrates the bone to a predetermined depth, the drill bit is removed from the passageway and a nerve ablation device 10, e.g., ablating probe 20, tube 60, or laser 80, is inserted into the passageway to ablate the intraosseous nerve as discussed above. Alternatively, a sleeve 30 having nerve ablation device 10 disposed within cavity 35 thereof, may be inserted into the passageway to ablate the intraosseous nerve.

It is to be understood that the invention is not limited to the exact details of construction, operation, exact materials, or embodiments shown and described, as obvious modifications and equivalents will be apparent to one skilled in the art. For example, while FIGS. 11*a*–11*b* and 12*a*–12*b* represent two preferred approaches, it will be appreciated by those of ordinary skill in the art that alternate approaches may be made depending upon the clinical setting. For example, the surgeon may elect not to cut or penetrate the vertebral bone but instead access, and ablate, the basivertebral nerves via, or adjacent, the central vascular foramen 209 at, or in close proximity to, the exit point of the basivertebral nerves from the bone. Moreover, while nerve ablation devices 10 and sleeves 30 described herein may be employed in accessing the basivertebral nerves and/or ablating these nerves, other devices and instruments not specifically described or illustrated herein may be included as part of the intraosseous nerve ablation systems 50 of the invention or used to perform the intraosseous nerve ablation methods described herein. Additionally, all of the ablating probes 20 and sleeves 30 illustrated and described herein may be modified as desired in terms of size, shape, and materials without departing from the scope and spirit of the present invention. Further, the shaft of the ablating probe may include a cavity containing an electrically conductive material, e.g., a wire, passing through the cavity to the tip of the shaft. Moreover, ablating probe 20 shown in FIGS. 3*a* and 3*b* may include drill threads 28 to facilitate creation of the passageway in the bone. Accordingly, the invention is therefore to be limited only by the scope of the appended claims.

What is claimed:

1. An ablating probe for ablating intraosseous nerves comprising:
    a shaft formed from an electrically conductive material, the shaft having a first end, a second end, and a length defined therebetween, wherein the second end of the shaft is adapted to be operatively associated with an electrical power source, the first end is adapted for creating a passageway in a bone thereby providing access to at least one of the intraosseous nerves, and a portion of the length of the shaft includes an insulating layer disposed thereon, the portion of the length of the shalt including the insulating layer disposed thereon having at least one drill thread disposed thereon in proximity to the first end; and
    a tip disposed at the first end, the tip being formed from an electrically conductive material.

2. The ablating probe for ablating intraosseous nerves of claim 1, wherein the shaft includes at least one drill thread disposed along the shaft in proximity to the first end, and the second end is adapted to be operatively associated with a drill.

3. The ablating probe for ablating intraosseous nerves of claim 1, wherein the shaft includes at least one handle.

4. The ablating probe for ablating intraosseous nerves of claim 1, wherein the tip is blunted.

5. The ablating probe for ablating intraosseous nerves of claim 1, wherein the tip is pointed.

6. The ablating probe for ablating intraosseous nerves of claim 1, wherein the second end is adapted to be operatively associated with a drill.

7. An ablating probe for ablating intraosseous nerves comprising:
    a shaft having a first end, a second end, a length defined therebetween, and at least one cavity, wherein the second end of the shaft is adapted to be operatively associated with a fluid source and the first end is adapted for creating a passageway in a bone, thereby providing access to at least one of the intraosseous nerves; and
    a tip disposed at the first end.

8. The ablating probe for ablating intraosseous nerves of claim 7, wherein the shaft includes at least two cavities.

9. The ablating probe for ablating intraosseous nerves of claim 7, wherein the tip is blunted.

10. The ablating probe for ablating intraosseous nerves of claim 7, wherein the tip is pointed.

11. The ablating probe for ablating intraosseous nerves of claim 7, wherein the shaft includes at least one handle.

12. An intraosseous nerve ablation system comprising:
    at least one nerve ablating device; and
    at least one sleeve;
    wherein the at least one sleeve is adapted for creating at least a portion of a passageway in a bone, thereby providing access to the intraosseous nerve.

13. The intraosseous nerve ablation system of claim 12, wherein the at least one nerve ablating device is an ablating probe having a shaft, the shaft having a first end including a tip formed from an electrically conductive material, a second end adapted to be operatively associated with an electrical power source, and a length defined between the first end and the second end.

14. The intraosseous nerve ablation system of claim 12, wherein the at least one nerve ablating device is an ablating probe having a shaft, the shaft having a first end, a second end adapted to be operatively associated with a fluid source, a length defined between the first end and the second end, and at least one cavity.

15. The intraosseous nerve ablation system of claim 12, wherein the at least one nerve ablating device is a laser.

16. The intraosseous nerve ablation system of claim 12, wherein the intraosseous nerve ablation system includes two sleeves.

17. The intraosseous nerve ablation system of claim 12, wherein the at least one sleeve includes a first end having an edge surface, a second end, a length defined between the first end and the second end, and a cavity.

18. The intraosseous nerve ablation system of claim 17, wherein the edge surface is serrated.

19. The surgical system for ablating intraosseous nerves of claim 17, wherein the edge surface is pointed.

20. A method of ablating an intraosseous nerve comprising the steps of:
   providing a nerve disposed within a bone and at least one ablating device having a sleeve adapted for creating at least a portion at a passageway in a bone;
   using the sleeve to create at least a portion of the passageway in the bone, thereby providing access to the intraosseous nerve;
   inserting the at least one ablating device into the passageway; and
   activating the at least one ablating device, thereby ablating the intraosseous nerve.

21. The method of claim 20, wherein the at least one ablating device is activated by transmitting electricity through the at least one ablating device.

22. The method of claim 20, wherein the at least one ablating device is activated by transmitting a fluid into, or through, the at least one ablating device.

23. The method of claim 20, wherein the at least one ablating device is an ablating probe and at least a portion of the passageway is created in the bone by the ablating probe.

24. The method of claim 20, wherein at least a portion of the passageway is created in the bone by a sleeve having at least one cavity and the at least one ablating device is inserted into the cavity of the sleeve and through the passageway until the at least one ablating device contacts, or is in close proximity to, the intraosseous nerve.

25. The method of claim 20, wherein the intraosseous nerve is a basivertebral nerve having an exit point.

26. The method of claim 25, wherein the basivertebral nerve is ablated at, or in close proximity to, the exit point.

27. The method of claim 20, wherein the at least one ablating device is inserted into the passageway until the at least one ablating device contacts, or is in close proximity to, the intraosseous nerve.

28. A method of ablating an intraosseous nerve comprising the steps of:
   providing a nerve disposed within a bone and an ablating device, the ablating device having a shaft formed from an electrically conductive material, the shaft having a first end, a second end, and a length defined therebetween, wherein the second end of the shaft is adapted to be operatively associated with an electrical power source, the first end is adapted for creating a passageway in a bone thereby providing access to at least one of the intraosseous nerves, and a portion of the length of the shaft includes an insulating layer disposed thereon, the portion of the length of the shaft including the insulating layer disposed thereon having at least one drill thread disposed thereon in proximity to the first end;
   creating a passageway in the bone, thereby providing access to the intraosseous nerve;
   inserting the ablating device into the passageway until the ablating device contacts, or is in close proximity to, the intraosseous nerve; and
   activating the ablating device, thereby ablating the intraosseous nerve.

29. The method of claim 28, wherein the ablating device is activated by transmitting electricity through the ablating device.

30. The method of claim 29, wherein at least a portion of the passageway is created in the bone by the ablating device.

31. The method of claim 29, wherein at least a portion of the passageway is created in the bone by a sleeve having at least one cavity and the ablating device is inserted into the cavity of the sleeve and through the passageway until the ablating device contacts, or is in close proximity to, the intraosseous nerve.

32. The method of claim 29, wherein the intraosseous nerve is a basivertebral nerve having an exit point.

33. The method of claim 32, wherein the basivertebral nerve is ablated at, or in close proximity to, the exit point.

34. The method of claim 28, wherein the intraosseous nerve is a basivertebral nerve having an exit point.

35. The method of claim 34, wherein the basivertebral nerve is ablated at, or in close proximity to, the exit point.

36. A method of ablating an intraosseous nerve comprising the steps of:
   providing a nerve disposed within a bone and an ablating device, the ablating device having a shaft, the shaft having a first end, a second end, a length defined therebetween, and at least one cavity, wherein the second end of the shaft is adapted to be operatively associated with a fluid source and the first end is adapted for creating a passageway in a bone thereby providing access to the intraosseous nerve;
   creating a passageway in the bone, thereby providing access to the intraosseous nerve;
   inserting the ablating device into the passageway until the ablating device contacts, or is in close proximity to, the intraosseous nerve; and
   activating the ablating device by transmitting a fluid into, or through, the ablating device, thereby ablating the intraosseous nerve.

37. The method of claim 36, wherein at least a portion of the passageway is created in the bone by the ablating device.

38. The method of claim 36, wherein at least a portion of the passageway created in the bone by a sleeve having at least one cavity and the ablating device is inserted into the cavity of the sleeve and through the passageway until the ablating device contacts, or is in close proximity to, the intraosseous nerve.

39. The method of claim 36, wherein the intraosseous nerve is a basivertebral nerve having an exit point.

40. The method of claim 39, wherein the basivertebral nerve is ablated at, or in close proximity to, the exit point.

41. A method of ablating a basivertebral nerve having an exit point comprising the steps of:
   providing a basivertebral nerve disposed within a bone and an ablating device, the ablating device having a shaft, the shaft having a first end, a second end, a length defined therebetween, and at least one cavity, wherein the second end of the shaft is adapted to be operatively associated with a fluid source and the first end is adapted for creating a passageway in a bone thereby providing access to the basivertebral nerve;

creating a passageway in the bone, thereby providing access to the basivertebral nerve;

inserting the ablating device into the passageway until the ablating device contacts, or is in close proximity to, the basivertebral nerve; and activating the ablating device, thereby ablating the basivertebral nerve.

42. The method of claim 41, wherein the basivertebral nerve is ablated at, or in close proximity to, the exit point.

43. A method of ablating a basivertebral nerve comprising the steps of:

providing a basivertebral nerve disposed within a vertebrae and at least one ablating device;

creating a passageway in the vertebrae, thereby providing access to the basivertebral nerve;

disposing the at least one ablating device into the passageway; and activating the at least one ablating device, thereby ablating the basivertebral nerve.

44. The method of claim 43, wherein the basivertebral includes an exit point and the basivertebral nerve is ablated at, or in close proximity to, the exit point.

* * * * *